United States Patent [19]

Ruggiero et al.

[11] Patent Number: 4,954,433

[45] Date of Patent: Sep. 4, 1990

[54] METHOD FOR THE IMMUNOLOCALIZATION OF ANTIGENS WITH THE USE OF ANTIBODIES DIRECTED AGAINST EPITOPES OF NON-GLUCIDIC NATURE

[75] Inventors: Paolo Ruggiero, Siena; Roberto Petracca, Monteroni D'Arbia, both of Italy

[73] Assignee: Sclavo S.p.A., Siena, Italy

[21] Appl. No.: 239,642

[22] Filed: Sep. 2, 1988

[30] Foreign Application Priority Data

Sep. 4, 1987 [IT] Italy ................................ 21792 A/87

[51] Int. Cl.$^5$ ............................................. G01N 33/535
[52] U.S. Cl. ...................................... 435/7; 435/810;
436/513; 436/548; 436/825; 436/827
[58] Field of Search ................... 435/7, 810; 436/827,
436/825, 513, 548, 808, 175

[56] References Cited

U.S. PATENT DOCUMENTS 4,289,747  9/1981  Chu ........................................ 424/1

FOREIGN PATENT DOCUMENTS 0155082 11/1980 German Democratic Rep. .

Primary Examiner—Esther M. Kepplinger
Assistant Examiner—Laurie A. Scheiner
Attorney, Agent, or Firm—Oblon, Spivak, McClelland, Maier & Neustadt

[57] ABSTRACT

A method is disclosed for the immunolocalization of epitopes of non-glucidic nature, in cellular cultures, in tissue slices, or immobilized on such supports as nitrocellulose, by means of the incubation of the sample with specific antibodies for the antigen to be immunolocalized, belonging to the class of the IgM's, and sequential treatment of concanavalin A and with an enzymatic marker capable of binding with concanavalin A, such as, e.g., peroxidase. The method comprises, before the incubation, a suitable treatment of the sample under test, e.g., with periodic acid, in order to prevent concanavalin A from binding with the carbohydrates present in the sample.

8 Claims, No Drawings

METHOD FOR THE IMMUNOLOCALIZATION OF ANTIGENS WITH THE USE OF ANTIBODIES DIRECTED AGAINST EPITOPES OF NON-GLUCIDIC NATURE

The object of the present invention is a method for the immonoidentification or immunolocalization of epitopes of non-glucidic nature.

In particular, the method according to the present invention, which is based on the capability of concanavalin A of very strongly binding with the immunoglobulins of IgM type, can be used for the immunolocalization of epitopes of non-glucidic nature in the cellular cultures and in slices of tissue, and also for the identification of determined antigens in the biological fluids and in tissular or cellular extracts, after the preliminary immobilization of such substances on an inert support.

The novel method makes it possible the system of detection of the antigen-antibody complex to be considerably simplified. The possibility of identifying particular antigens, or of localizing their presence in determined tissues by means of a highly antigen-antidbody reaction, is an extremely useful means both for an as precise and early diagnosis as possible of such pathologic forms, and from the viewpoint of an increase in basic knowledge relevant to the genesis of such pathologic forms; and, finally, for a verification of the efficacy of the therapy carried out.

The routine methods used in immunochemistry provide, in case the (so-said primary) antibodies specific for the investigated antigen are not directly "marked", for the use of rather complex detection systems, wherein a second, species-specific antibody (i.e., a "secondary antibody") is always present, which is conjugated with a so-said "marker" (fluorescent substances, enzymes, radioisotopes, biotin, and so forth). Such detection systems represent a critical point as regards both the good outcome of the investigation, in that possible aspecific reactions would completely distort the work, and the cheapness of the investigation system, in that to carry out a full set of operations of-whether primary or secondary-antibody modification, if one takes into account the cost thereof, and the extremely low yields to pure product, is not economically feasible.

Many attempts of use of lectins in the diagnostic field were made in the past.

For example, U.S. Pat. No. 4,298,689, discloses a test for *Neisseria gonorrhoeae*, which is carried out by using a lectin showing a high affinity for N-acetylglucosamine. In practice, according to such a patent, the sample to be analysed in placed into direct contact with the lectin and the possible presence of the reaction product on the cellular surface of the microorganism is used as an evidence of the presence of the same microorganism.

In a similar way, in U.S. Pat. No. 4,389,392, particular lectins are used, which combine with determined end saccharides, in order to evidence the presence of glycoproteins associated with certain tumor forms. The use is furthermore known of concanavalin A and of other lectins (LCH, PHA, RCA, and so forth), in a method for the differential diagnosis of cancer (EP-A-0 171 243), based on the determination of certain glycoantigens antigens present in the biological fluids of some cancer forms. The present of the different glyco-antigens is detected by means of the capability shown by these latter, of binding or less with the different lectins. In all these cases, anyway, no selective immunologic reactions are concerned, and such methods are therefore for an extremely limited use.

A different approach to the use of lectins is that of U.S. Pat. Nos. 4,289,747 and 4,371,515, wherein a lectin is conjugated with an immunoglobulin, and the affinity of lectin for the sugars is exploited, in order to immobilize the conjugate, and insolubilize it.

Recently, in patent literature (EP-A-41426 and DD-155082) methods of detection have beend disclosed, which use, as the either primary, or secondary, antibody, an antibody conjugated with a lectin, and, in particular with concanavalin A, and, as the detection system, peroxidase. As previously stated, the preparation of such an antibody-lectin conjugate presupposes the reaction, in one or two separate steps, of the antibody and of the lectin with a coupling agent, such as, e.g., glutaraldehyde or p-benzoquinone, and the purification of the obtained product, both which reaction involve a considerably decrease in yields.

Finally, in EP-A-166 623 application, a method is disclosed for the determination of glycoproteins, glycopeptides, carbohydrates or glycolipids by means of a first reaction through the immunologic reaction with an immobilized antibody and hence a determination by means of the non-specific reaction with a lectin conjugated with a marker. In this latter case too, the lectin is conjugated, by means of a true chemical reaction, with the marker before being used in the determination, with the problems relevant to the preparation of the conjugate, as above said. In both these latter references, the lectin is anyway used in order to determine the antigens containing a glucidic residue.

The present applicant has found now that, when in an immunochemical assay, specific antibodies are used, which belong to the class of IgM's, it is possible to detect the possible presence of the antigen-IgM antibody complex, in a very simple and cheap way, by treating the complex with concanavalin A, which forms a strong bond with the IgM, and then with a suitable enzymatic marker, containing an $\alpha$-D-glucose or $\alpha$-D-mannose group able to bind with concanavalin A, capable of producing, in the presence of a suitable enzymatic substrate, a characteristic coloured precipitate, easily appreciable by the naked-eye on inert supports, or as regards the tissue slices or the cellular cultures, under the microscope.

In this case, concanavalin A is hence used in the first step of the detection process, and interacts with the antibody, and not with the antigen, thus offering wide possibilities of use of this system in the determinazion of many antigens.

Extremely good results were obtained by using peroxidases as the marker, but according to an alternative route, other enzymes endowed with the above-reported requisites are regarded as suitable for such an use, with analogous results. Anyway, the use of the peroxidase yields the additional advantage that it has been deeply studied and optimized, so that from the relevant literature many methods are known in order to detect this enzyme (e.g., the classic method of diaminobenzidine (DAB), described by R. C. Graham and M. J. Karnovsky, in J. Histochem. Cytochem., 14 291-302 (1966), or the method as described bu J. S. Hanker et al. in Histochem. J., 9, 789-92 (1977), which uses p-phenylene-diamine and pyrocathecol as the reactant, as well as the method of 3-amino-9-ethyl-carbazole (AEC), described by R. C. Graham et al., in J. Histochem. Cytochem., 13, 150-2 (1965).

But, as known, inasmuch as concanavalin A has a great affinity for carbohydrates (J. Roth, Exp. Path. Suppl. 3, (1978), and B. A. J. Ponder, Immunocytochemistry, practical applications in pathology and biology, 129–42, John Wright & Sons (1983)), in order to prevent non-controllable interferences between the detection system and the carbohydrates possibly present in the test sample, the preliminary removal or masking these latter is necessary.

This can be carried out more advantageously by treating the sample with periodic acid, according to the methodology described by N. Beccari and V. Mazzi in "Manuale di Tecnica Microscopica (Handbook of Microscopy Technique)", pages 240–1, in order to oxidate the carbohydrates present in the test sample.

Alternative treatments can be developed by those skilled in the art, on the basis of the common knowledge in this field, and of the particular requirments of the technique used. The treatment with periodic acid makes it anyway possible, in case in order to detect concanavalin A peroxidase is used, the endogenous peroxidase to be also removed from the sample.

In case the presence of a particular antigen in a proteinic blend obtained from a biological fluid, or in the proteinic isolates obtained by fractionating such a blend, has to be detected, the elimination of the possible interferences between concanavalin A and the possible present carbohydrates, can be alternatively obtained by causing the proteinic blend to flow over a column containing immobilized concanavalin A, and subsequently analysing the effluent mixture, possibly fractionated and suitable immobilized on an inert solvent.

This method necessarily uses specific antibodies belonging to the class of the immunoglobulins IgM's, in that only the IgM's form a strong enough bond with concanavalin A, such as to secure the extremely good experimental results obtained.

Between the IgG's and concanavalin A, in fact, a high affinity does not exist (cfr. J. Arends, Methods in Enzymology, Vol. 73, 166–175) and, in that case, it is necessary to conjugate the IgG's with concanavalin A by means of a coupling agent (reference is made to the above cited patents).

Typically, monoclonal IgM's are used. In fact, it is knopwn that the IgM's are the immunoglobulins which are obtained as the primary response to the introduction of the antigen in the body, viz., it is the immunoglobulins which are obtained during the first steps of the immunization (F. A. Murphy et al., J. Infect. Dis., 116, 99 (1966)) and are therefore present in an extremely reduced amount in the serum of the animal. Therefore, it is not economically advantageous to obtain these specific antibodies by immunizing the animal, in that the animal must be sacrificed when its antibody response is still extremely reduced.

The techniques for the production of monoclonal antibodies are anyway widely known (see, e.g., C. Milstein et al., in Nature, 256, 495–497 (1975); C. Milstein et al., in Cell. Bio. Int. Rep., 3, 1–16 (1979); C. Milstein, in Sci. Amer., 243, 56–64 (1980); and A. J. McMichael et al., in "Monoclonal Antibodies in Clinical Medicine", Academic Press (1982), and it is not necessary to repeat them herein; furthermore, some of such specific antibodies are available on the market.

The method according to the present invention is generally applicable in the immunochemical, immunocytochemical and immunohistochemical techniques. Obviously, it cannot be used in the determination of antigens in case the antibody is directed against an epitope of glucidic nature, but, on the contrary, it can be also used in the determination of some antigens of a different type. It could be used, e.g., for the determination of some "haptens", such as, e.g., the non-peptidic steroid hormones, e.g., progesterone, estradiol testosterone, and so forth, the thyroid hormones, e.g., thyroxine and triiodothyronine, some antibiotics, vitamins, pesticides, and so forth, on condition that against them monoclonal antibodies belonging to the class of IgM's are obtained, and that the preliminary treatment designed to eliminate the undesired concanavalin A binding does not alter the structure thereof, such as to eliminate also the antigen-antibody binding.

In practice, the method of immunolocalization of epitopes of non-glucidic nature according to the present invention can be advantageously used on cryostatic slices of tissue on slices of tissue fixed in formalin or in another fixative agent, and included inside paraffin, on suitably fixed cellular smears or preparations from cytocentrifuge, on proteinic blends immobilized in inert supports, such as nitrocellulose, or on proteinic isolates obtained by fractionating such blends. Inasmuch as the primary use of such a method is anyway in the field of immunohistochemistry, in the following the procedure is disclosed in greater detail, which is advantageously followed for immunolocalization of antigens in tissue slices.

On the basis of the information supplied in the following, and of what is known from the technical literature on this subject, anyone having an average skill in this field will be surely capable of applying the immunochemical determination method according to the present invention to different substrates.

For the preparation of the slices of tissue to be submitted to the immunochemical test, the tissues are submitted to the conventional steps of fixation and inclusion, according to the methods known in the art.

According to the method of the present invention, after removing paraffins from the slices, or, in case of cryostatic tissue slices, after re-hydrating them, the tissue slices are submitted to a treatment with a diluted solution of periodic acid, having the purpose of oxidating the sugars possibly present in the tissue, and thus preventing concanavalin A from binding with them. In this step, a 1% solution of periodic acid can be advantageously used, with the treatment being carried out at room temperature, and being continued for about 15 minutes. Of course, the concentration of the acid can be increased, or decreased (e.g., a concentration comprised within the range of from 0.5 to 1.5% can be used), and the treatment time can be proportionally extended or shortened. In any case, adapting the treatment to the type of sample under test is necessary.

In practice, it is advantageous to verify, before carrying out the immunolocalization, the efficacy of the treatment on the investigated material, by testing different concentrations of periodic acid, or different treatment times on several samples of the same material, and varifying—by means of a treatment of concanavalin A and peroxidase—that the binding of concanavalin A is actually eliminated. The sample is then thoroughly washed with water, and then with a buffer solution, suitable for causing the immunologic reaction to take place, generally a phosphate buffer-saline (PBS) having a pH value of 7.2–7.4. The sample is then treated with the antibody belonging to IgM class, specific for the angtigen which one wants to determine, under such conditions as commonly used in immunohistochemical methods, which are the suitable conditions for enabling the immunologic reations between both partners to occur.

According to such conditions, an incubation is carried out at a temperature comprised within the range of from 4° C. to room temperature, for a time normally comprised within the range of from 10 minutes to 48 hours, according to the titre and the dilution of the antibody.

After a further washing with the buffer, the tested sample is washed with a diluted solution of concanavalin A. As the solvent for concanavalin A, the same buffer solution is advantageously used, which is used in the previous step, preferably with the addition of some salts of bivalent metals (calcium, magnesium and manganese), which serve to secure a good operation of concanavalin A, each sub-unit of which contains a $Ca^{++}$ ion and an $Mn^{++}$ ion. Normally, besides these bivalent ions, which will be present in extremely small amounts (5–15 $\mu$mol/liter), the buffer solution will furthermore contain also extremely small amounts ($\leq 1\%$) of a non-ionic surfactant.

Extremely good results can be obtained by using concentrations of concanavlin A comprised within the range of from 5 to 20 $\mu$g/ml.

In general, an incubation of 1 hour at room temperature is enough in order to achieve the complete binding of concanavalin A to IgM. Both the treatment time and the concentration can be anyway changed and adjusted according to the requirements, anyway taking into account that higher concentrations than as disclosed can originate an undesired background.

At the end of the incubation, a further washing is carried out in order to remove unbound concanavalin A, and the same is then treated with a dilute solution of the enzyme used as the marker, preferably peroxidase.

Inasmuch as concanavalin A is a tetramer, and therefore has four binding sites for the glucidic residues, only one of which is engaged in the binding with the IgM, still three sites for binding the peroxidase are available per each molecule of concanavalin A. Good results were obtained by using solutions of peroxidase in the same buffer system as used for concanavalin A, having a concentration comprised within the range of from 15 to 60 $\mu$g/ml. In this case too, the same considerations as regards the concentration and the treatment time, as above stated for concanavalin A, hold true.

Also in this case, an incubation time of approximately one hour is generally enough in order to have the binding of the peroxidase to the free sites of bound concanavalin A.

The conventional washes, in order to remove the unbound enzyme, and then the incubation with a suitable enzyme substrate makes it furthermore possible the antigen to be immunolocalized, by means of the formation of a coloured precipitate.

The results which are obtained by means of the method according to the present invention are comparable to those which are obtained by means of the most sophisticated and sensitive immunochemical methods known from the relevant literature, or available from the market, such as the method of the indirect immunoperoxidase, which, after the specific antibody, uses a second species-specific antibody conjugated with the peroxidase, or the ABC (avidin-biotin complex) commercial system which, after the specific antibody, sequentially uses a second species-specific antibody conjugated with biotin, then a pre-constituted complex of avidin and biotinylated peroxidase, thus the detection and amplification of the signal being obtained.

If desired, after the incubation of the sample with concanavalin A, the signal can be detected or amplified by means of any know technique, which involves the use of avidin, such as, e.g., in the ABC commercial system, in that avidin is a glycoprotein with which concanavalin A can bind.

The greater simplicity of the method according to the present invention, which, on the contrary, uses one single specific antibody, as compared to the methods known from the prior art, such as, e.g., the above discussed methods, is immediately evident from the following examples.

EXAMPLE 1

Immunolocalization of Vimentin

Vimentin is a protein having a molecular weight of 58,000 daltons, which constitutes the intermediate filaments of the tissue of mesenchymal origin, excluding the muscular cells. The identification of vimentin makes it possible the mesenchimal origin of melanomas, histiocytomas and sarcomas to be attributed. Vimentin is a cytoskeletal marker, the synthesis of which is acquired by all the epithelial cells in culture. Furthermore, epithelial tumors can express vimentin and cytokeratins.

The Antibody

The monoclonal anti-vimentin antibody is a supernatant from a hybridoma culture, belonging to IgM class, and is a product traded by Sclavo.

The Immunohistochemical Test

Slices of the tissue, fixed in formalin, and included in paraffin, are deprived of paraffin by means of the conventional methods (three changes of 10 minutes in xylene, rehydration in a series of alcoholic solutions, from 95 to 50°, then washing with distilled water).

The slides are dipped in (or on the slices drops are added of) a solution of periodic acid at 1% in distilled water at room temperature. Ten minutes later, the samples are washed a plurality of times with distilled water and then with PBS (Phosphate Buffer-Saline) (a solution in distilled water containing $Na_2HPO_4$ (0.9 g/l), $KH_2PO_4$ (0.2 g/l), NaCl (8 g/l), and KCL (0.2 g/l)).

A solution of the antibody in the reconstitution buffer (PBS) at a dilution comprised within the range of from 1:20 to 1:50 is added, and is allowed to incubate for 30–60 minutes at room temperature.

The samples are then washed three times with PBS containing calcium, magnesium and manganese ions at a 10-$\mu$M concentration (PBS++) and 0.5% of Triton[R]×100.

The samples are then incubated for one hour at room temperature with a solution of concanavalin A at a concentration of 10 $\mu$g/ml in PBS++.

The samples are washed three times with PBS ++ and are subsequently incubated for one hour at room temperature with peroxidase (horseradish peroxidase (type VI)—by Sigma Chemical Company) at a concentration of 50$\mu$g/ml.

The samples are washed three times with small aliquots of PBS++ in order to eliminate any non-bound peroxidase. The incubation with a solution of 3amino-9-ethyl-carbazole and $H_2O_2$ in DMF according to the method by Graham, Ludholm and Karnovsky for 10–20 minutes yields, in the presence of vimentin, a coloured precipitate clearly detectably under the microscope.

EXAMPLE 2

The above disclosed technique can be also applied in order to detect the antigen in Western blot.

In this case, the mixture which contains the antigen is denaturated, and the polypeptides which constitute it are separated by electrophoresis on a polyacrylamide gel containing sodium dodecyl-sulphate. At the end of the run, the material is transferred by electrophoresis from the gel to a nitrocellulose sheet. The nitrocellulose sheet is submitted to a treatment with a solution of periodic acid at 1% for approximately 30 minutes, and is then saturated with a solution of bovine serum albumin (BSA) at 3% in PBS; then a procedure analogous to that reported in Example 1 is followed, by incubating for 2-3 hours with an anti-vimentin antibody belonging to IgM class diluted at a 1:5 dilution ratio, then with a solution of concanavalin A, with a solution of peroxidase as the enzymatic marker, and then with the suitable enzymatic substrate. The methodology used in this latter step is the same as used for detecting the glycoproteins on nitrocellulose (see J. S. Clegg, Analytical Biochemistry, 127, 389-94, 1982).

Example 3

Immunolocalization of a specific antigen of the respiratory cilium

The vibratile cilia are constituted by at least 200 different polypetides; the absence of one, or of a group, of them can cause pathologic alterations in the same cilium.

The methods used in Examples 1 and 2 for the determination of vimentin are substantially repeated by using, instead of the anti-vimentin antibody, an A.M. 3.12 monoclonal antibody, belonging to the class of the IgM's, directed against a polypetide having a molecular weight of approximately 300,000 daltons, specific of the respiratory cilium (Mencarelli and co-workers, in "Biology of Reproduction and Cell Motility in Plant and Animals", Compilers: M. Cresti and R. Dallai, 1986, pages 75-80).

A further object of the present invention is a kit for the immunolocalization of antigens of non-glucidic nature, characterized in that it contains the following compounds:

(a) an antibody belonging to the class of IgM's, specific against the antigen to be determined,
(b) concanavalin A,
(c) an enzymatic marker containing a glucidic residue capable of being recognized by concanavalin A, and
(d) a suitable substrate for the detection of the enzymatic marker used.

According to a preferred form of practical embodiment, such a kit will furthermore contain periodic acid, to be used in the initial pre-treatment, aiming at preventing concanavalin A from binding with molecules of glucidic nature present in the sample.

According to a still more preferred form of practical embodiment, such a kit will contain peroxidase as the enzymatic marker.

We claim:

1. Method for the immunolocalization of antigens by means of the use of antibodies directed against epitopes of non-glucidic nature, which comprises:
   (a) submitting the sample to a treatment for modifying or masking any possibly present glucidic residues,
   (b) treating the sample with specific antibodies for the antigen to be determined, belonging to the class of the IgM's under conditions, and for a time sufficient for the immunologic reaction to take place,
   (c) treating the sample with concanavalin A under conditions, and for a time sufficient for the binding between the molecules of IgM bound to the antigen, and concanavalin A, to take place,
   (d) treating the sample with the enzymatic marker peroxidase, which contains a glucidic residue recognizable by concanavalin A, and
   (e) incubating the enzymatic marker with a substrate specific for peroxidase wherein a color development is an indication of the presence of said antigens containing epitopes of non-glucidic nature.

2. Method according to claim 1, wherein the (a) step is carried out by treating the sample with a solution of periodic acid having a concentration within the range of from 0.5 to 1.5%.

3. Method according to claim 1, wherein the specific immunoglobulins belonging to the class of the IgM's, used in the (b) step are monoclonal.

4. Method according to claim 1, wherein the (c) step is carried out by using a solution of concanavalin A having a concentration within the range of from 5 to 20 µg/ml.

5. Method according to claim 2, wherein the peroxidase solution of (d) which has a concentration within the range of from 15 to 60 µg/ml.

6. Method according to claim 1, wherein the determination is carried out on slices of tissues, cell cultures, or preparations from cytocentrifuge, or on preparations of antigen immobilized on an inert support.

7. Kit for the immunolocalization of epitopes of non-glucidic nature comprising, the following components:
   (a) an antibody belonging to the class of IgM's, specific against the antigent to be determined,
   (b) concanavalin A,
   (c) the enzymatic marker peroxidase, which contains a glucidic residue capable of being recongnized by concanavalin A, and
   (d) substrate specific for peroxidase 8. Kit according to claim 7, containing periodic acid as a further component.

* * * * *